(12) United States Patent
Nevins (10) Patent No.: US 9,943,413 B2
(45) Date of Patent: Apr. 17, 2018

(54) REVISION STEPPED TIBIAL IMPLANT

(71) Applicant: Russell Nevins, Las Vegas, NV (US)

(72) Inventor: Russell Nevins, Las Vegas, NV (US)

( * ) Notice: Subject to any disclaimer, the term of this patent is extended or adjusted under 35 U.S.C. 154(b) by 15 days.

(21) Appl. No.: 15/186,350

(22) Filed: Jun. 17, 2016

(65) Prior Publication Data

US 2017/0128217 A1 May 11, 2017

Related U.S. Application Data

(63) Continuation of application No. 15/011,402, filed on Jan. 29, 2016.

(60) Provisional application No. 62/110,410, filed on Jan. 30, 2015.

(51) Int. Cl.
*A61F 2/38* (2006.01)
*A61F 2/30* (2006.01)

(52) U.S. Cl.
CPC .......... *A61F 2/389* (2013.01); *A61F 2/30734* (2013.01); *A61F 2/3868* (2013.01); *A61F 2002/3085* (2013.01); *A61F 2002/30233* (2013.01); *A61F 2002/30235* (2013.01); *A61F 2002/30324* (2013.01); *A61F 2002/30428* (2013.01); *A61F 2002/30738* (2013.01); *A61F 2002/30897* (2013.01); *A61F 2220/0033* (2013.01); *A61F 2220/0058* (2013.01); *A61F 2250/0006* (2013.01); *A61F 2250/0064* (2013.01)

(58) Field of Classification Search
CPC .... A61F 2/389; A61F 2/3868; A61F 2/30734; A61F 2002/30233
See application file for complete search history.

(56) References Cited

U.S. PATENT DOCUMENTS

| | | |
|---|---|---|
| 5,613,970 A | 3/1997 | Houston et al. |
| 7,291,174 B2 | 11/2007 | German et al. |
| 8,366,782 B2 | 2/2013 | Wright |
| 8,382,849 B2 | 2/2013 | Thomas |
| 8,424,183 B2 | 4/2013 | Thomas |
| 8,480,751 B2 | 7/2013 | Metzger et al. |
| 2004/0049286 A1 | 3/2004 | German et al. |
| 2004/0073315 A1 | 4/2004 | Justin et al. |
| 2006/0030945 A1 | 2/2006 | Wright |
| 2009/0088861 A1 | 4/2009 | Tuke et al. |
| 2010/0178194 A1 | 7/2010 | Broadley et al. |
| 2012/0310361 A1 | 12/2012 | Lubok et al. |
| 2013/0325136 A1 | 12/2013 | Thomas et al. |
| 2014/0081408 A1 | 3/2014 | Lieberman et al. |

(Continued)

FOREIGN PATENT DOCUMENTS

| | | |
|---|---|---|
| CN | 101601614 A | 6/2009 |
| EP | 0993807 B1 | 4/2005 |

(Continued)

*Primary Examiner* — Jason-Denise Stewart
(74) *Attorney, Agent, or Firm* — Weide & Miller, Ltd.

(57) ABSTRACT

A tibial implant having a stem and a tibial sleeve. The tibial sleeve having a proximal end and a distal end, where the proximal end includes an annular male portion. The tibial implant also includes an offset ring having a central bore that is offset from the center of the offset ring, where the bore of the offset ring receives the annular male portion of the tibial sleeve. The tibial implant further includes a base plate having a proximal end and a distal end, where the distal end of the base plate forms a female portion, and the female portion receives both the offset ring and the male portion of the tibial sleeve.

40 Claims, 10 Drawing Sheets

(56) References Cited

U.S. PATENT DOCUMENTS

| | | |
|---|---|---|
| 2014/0081409 A1 | 3/2014 | James et al. |
| 2014/0081410 A1 | 3/2014 | Lieberman et al. |
| 2014/0081411 A1 | 3/2014 | Lieberman et al. |

FOREIGN PATENT DOCUMENTS

| | | |
|---|---|---|
| EP | 2130516 A1 | 12/2009 |
| EP | 2394607 A1 | 12/2011 |
| EP | 2130516 B1 | 3/2014 |
| EP | 2710969 A1 | 3/2014 |
| EP | 2710980 A1 | 3/2014 |
| EP | 2710981 A1 | 3/2014 |

REVISION STEPPED TIBIAL IMPLANT

CROSS-REFERENCE TO RELATED APPLICATIONS

This application is a continuation of U.S. patent application Ser. No. 15/011,402, filed Jan. 29, 2016, which claims the benefit of U.S. Provisional Patent Application Ser. No. 62/110,410, filed Jan. 30, 2015, which are hereby incorporated by reference herein in their entireties, including but not limited to those portions that specifically appear hereinafter, the incorporation by reference being made with the following exception: In the event that any portion of the above-referenced applications are inconsistent with this application, this application supercedes the above-referenced applications.

STATEMENT REGARDING FEDERALLY SPONSORED RESEARCH OR DEVELOPMENT

Not Applicable.

BACKGROUND

1. The Field of the Present Disclosure.

The present disclosure relates generally to knee joint prosthesis and more particularly to a revision tibial implant and method of utilizing and implanting the same.

2. Description of Related Art.

Conventionally a knee joint prosthesis can include a femoral implant and a tibial implant. The femoral implant and tibial implant are designed to be surgically implanted into the distal end of the femur and the proximal end of the tibia, respectively. The femoral implant is further designed to cooperate with the tibial implant in simulating the articulating motion of an anatomical knee joint.

These femoral and tibial implants, in combination with ligaments and muscles, attempt to duplicate natural knee motion as well as absorb and control forces generated during the range of flexion. In some instances however, it may be necessary to replace or modify an existing femoral and/or tibial implant. Such replacements are generally referred to as revision implants. It may be necessary for a revision implant to eliminate one or more motions, thereby increasing the level of restraint, in order to provide adequate stability. In this way, it may be desirable to provide a cruciate retaining (CR) revision knee, a fully constrained revision knee, a posterior stabilized (PS) revision knee or a hinged revision knee for example.

There are also circumstances when a fixed bearing implant must be changed out for a mobile bearing implant. While this change is possible, it can create added damage and deterioration of the remaining tibial bone due to the need to remove the tibial implant to replace it. Therefore, there is a need to enable a surgeon to change or modify an existing implant from a fixed bearing to a mobile bearing (or vice versa), without removing the tibial implant from the tibial bone, thus saving the integrity of the surrounding tibial bone.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

Applicant has discovered a novel apparatus and method for a revision tibial implant having modularity between a fixed and mobile bearing configuration.

Applicant's method of initially implanting and interchanging a revision stepped tibial implant is also discussed herein below. In an exemplary method, insertion of a tibial implant is accomplished by drilling or otherwise creating a cavity in the proximal end of a tibial bone. A stem is then inserted into the cavity such that the outer surface of the stem engages and contacts the surrounding bone.

The stem can then be threadedly engaged with a tibial sleeve, allowing the stem to be easily assembled with, or disengaged from, the tibial sleeve. This modularity between the stem and the tibial sleeve can enable a surgeon or user to customize the sizes of a stem and a tibial sleeve to accommodate the specific needs of each particular tibial implant.

On the distal end of the stem is a male threaded portion which can be threadedly mated with a female threaded portion located on the distal end of the tibial sleeve. This threaded engagement enables different sized tibial sleeves to mate with a variety of different sized stems.

The outer surface of the tibial sleeve can include tapered steps which can improve grafting with the surrounding bone of the tibia after the tibial sleeve is inserted into the tibial and threadedly attached to the stem. This improved grafting can better secure the tibial implant in place and reduce the likelihood of complications or failure stemming from the unintentional displacement of the tibial implant.

The tibial sleeve, can include an annular male portion having a central bore that is coaxial with the tibial sleeve. The male end can extend from the distal end of the tibial sleeve, and receive an offset ring which is designed and configured to fit securely around and be removably fixed to the male end of the tibial sleeve, via a friction fit, cold weld or other desired securement mechanism. Thus, after the tibial sleeve is connected to the stem, the offset ring is secured around the male end of the tibial sleeve. The offset ring is cylindrical in shape, having a substantially circular cross-section, but includes a bore that is offset from the central axis of the offset ring. The offset of the bore can be substantially zero, meaning the bore can be coaxial with the central axis of the offset ring.

A base plate can then be connected to tibial sleeve. The base plate can include, on the distal end, a female portion that includes a counter-sunk bore configured to receive the offset ring. The outer surface of the offset ring may be configured to engage and mate with the female portion of the base plate, such that the female portion is removably fixed to the offset ring via a friction fit, cold weld or other desired securement mechanism. The offset configuration of the bore within the offset ring may enable the base plate to be axially offset with respect to the tibial sleeve and stem. The removable engagement between the base plate and the offset ring can enable a surgeon or user to remove the base plate from the tibial sleeve, and substitute a different base plate and/or offset ring, without having to remove the tibial sleeve and stem from the tibial bone. The resulting modularity between the offset ring and base plate, with respect to the tibial sleeve, can enable a surgeon or user to change or modify the size, positioning (relative to the tibial sleeve and stem), or type of base plate, without also removing tibial sleeve and stem.

This modularity can provide significant benefits, for example, after inserting the tibial implant, a surgeon or user can change and replace a base plate and/or offset ring if the ideal size or positioning of the base plate needs to be modified, without removing the stem and tibial sleeve from the patient which can cause unwanted damage to the tibial bone. Another example of the benefits of modularity of the base plate and offset ring with respect to the tibial sleeve can occur when changes or repairs need to be made to a preexisting tibial implant. In this case a surgeon or user can exchange the preexisting base plate with a different base plate, to accommodate a new or different condition, or repair a broken base plate, all without removing the stem and tibial sleeve, saving further damage to the tibial bone.

The proximal end of the base plate can be configured with a counter-sunk tray portion having a substantially planar central surface with a central bore. The tray of the base plate may be configured to receive a platform. Thus, after the base plate has been secured to the tibial sleeve (about the offset ring and male end of the tibial sleeve) a platform may be secured to the base plate. The platform can include various features or embodiments to accommodate various levels of restraint needed by a patient, for example, alternative platforms can be designed and used to accommodate a Posterior Cruciate (PS), Cruciate Retaining (CR), Constrained Condylar Knee (CCK) or a hinge type platform.

The platform can also include a spike that extends from a base of the platform in a proximal direction, and a post that extends in an opposite distal direction from the spike. As the platform is secured to the base plate, the post extends through the bore of the base plate, through the offset ring and into the central bore of the male end of the tibial sleeve. The central bore of the tibial sleeve can be sized to retain the post and provide strength and stability to the platform, via the post. The post is then removable from the central bore of the tibial sleeve, to enable simple and easy removal of the platform to accommodate a replacement platform, without requiring a corresponding removal of the tibial sleeve and stem.

The platform is configured to engage with a corresponding femoral implant (not shown), thus completing a total knee replacement implant. The disclosed tibial implant can be a fixed bearing system, where the platform is fixed to the tray, such that the platform can not rotate with respect to the tray or base plate. In the fixed bearing configuration the platform can be cold welded to the tray or fixed using another desired fixation mechanism.

Alternatively, the disclosed tibial implant can be a mobile bearing system, where the platform is rotatable with respect to the tray and base plate. When the post of the platform is inserted into the base plate and tibial sleeve, a bushing can be utilized to receive the post. The bushing can be inserted into the bore of the base plate and the central bore of the tibial implant. The bushing can be sized to the central bore of the tibial sleeve without any lateral movement, thus providing lateral stability to the post and platform, while still maintaining smooth rotatability of the platform with respect to the base plate and tibial sleeve. The bushing can reduce the friction of the rotating post, in a mobile bearing configuration, thus improving the life and functionality of both the post and the tibial sleeve.

In the disclosed method of changing or modifying a previously used tibial implant, the surgeon or user can readily remove the platform and or base plate, due to the modularity discussed above, in exchange for a different size or type of platform and/or base plate. For example, if a fixed bearing implant, according to the disclosed embodiment, was inserted into a patient's tibial bone, a surgeon could then remove the fixed bearing platform, and base plate if necessary, and replace it with a mobile bearing platform and base plate, without removing the tibial sleeve and or stem.

Figure 1:
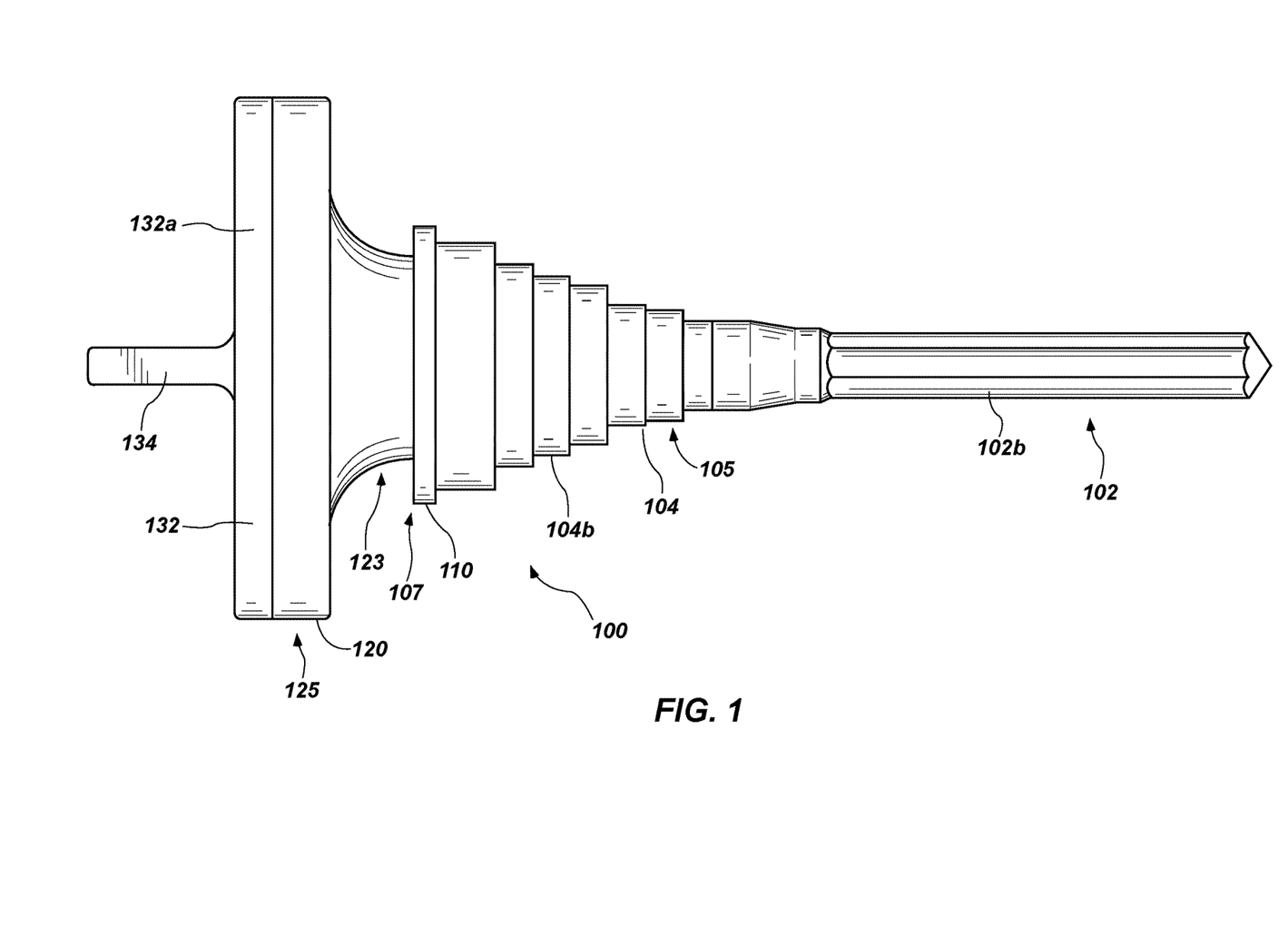
FIG. 1 is a side view of an embodiment of the tibial implant of the present disclosure.
Figure 2:
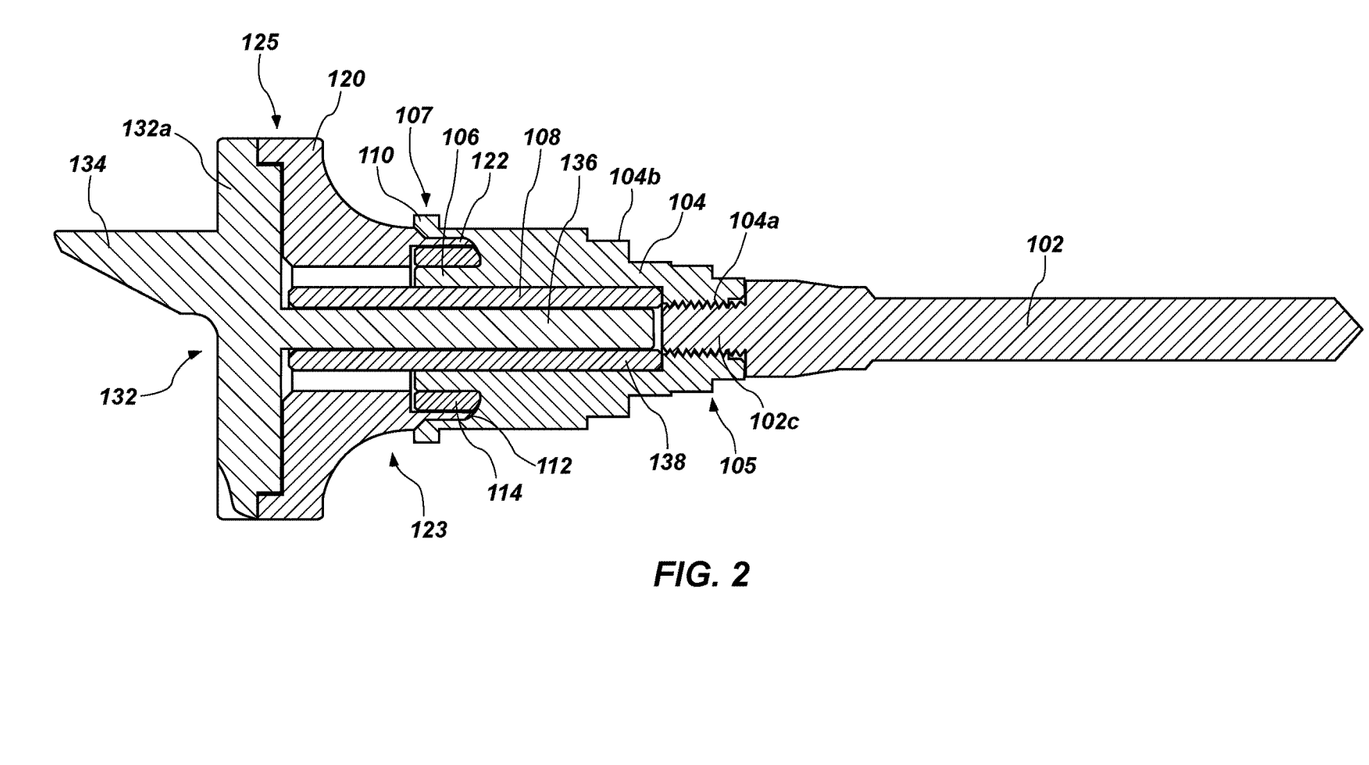
FIG. 2 is a cross-sectional side view the embodiment of FIG. 1.
Figure 3:
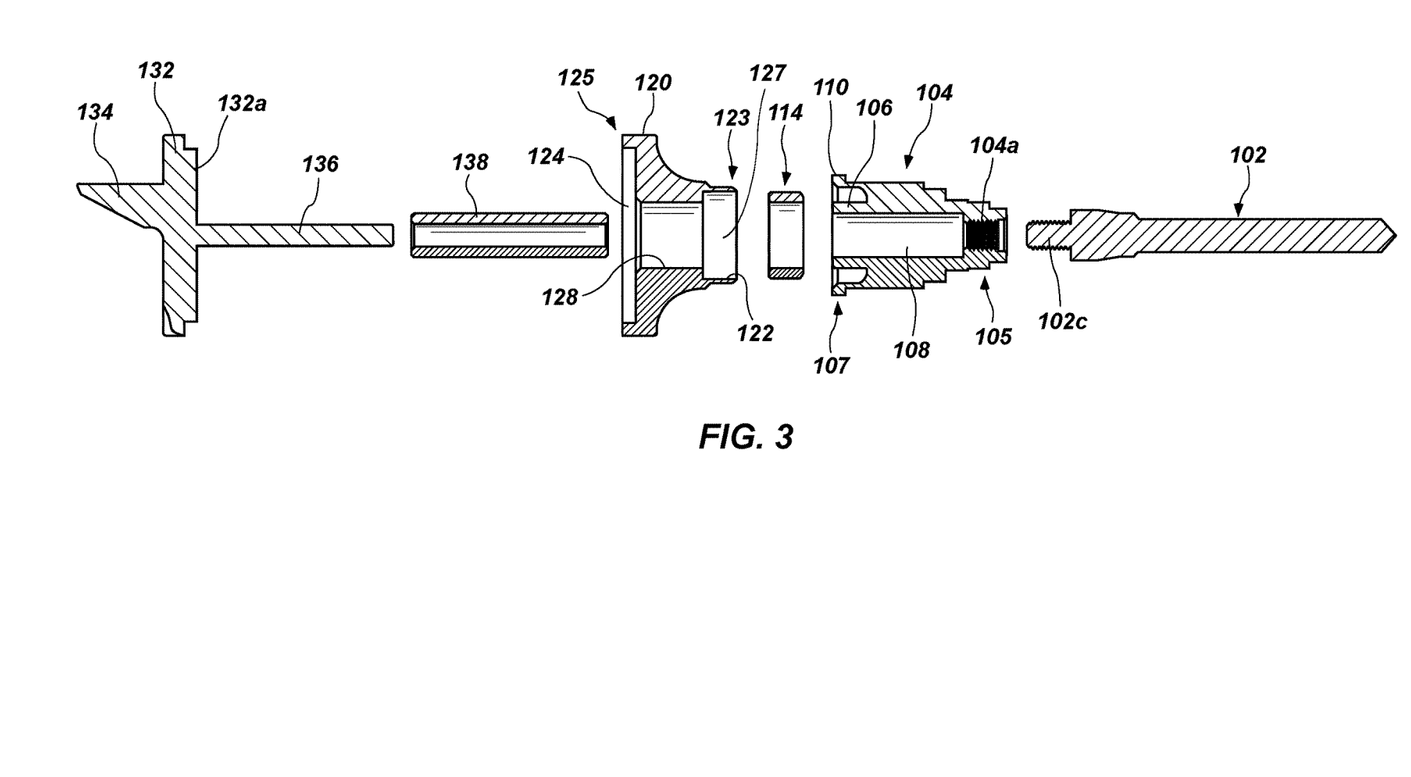
FIG. 3 is an exploded cross-sectional side view of the embodiment of FIG. 1.
Figure 4:
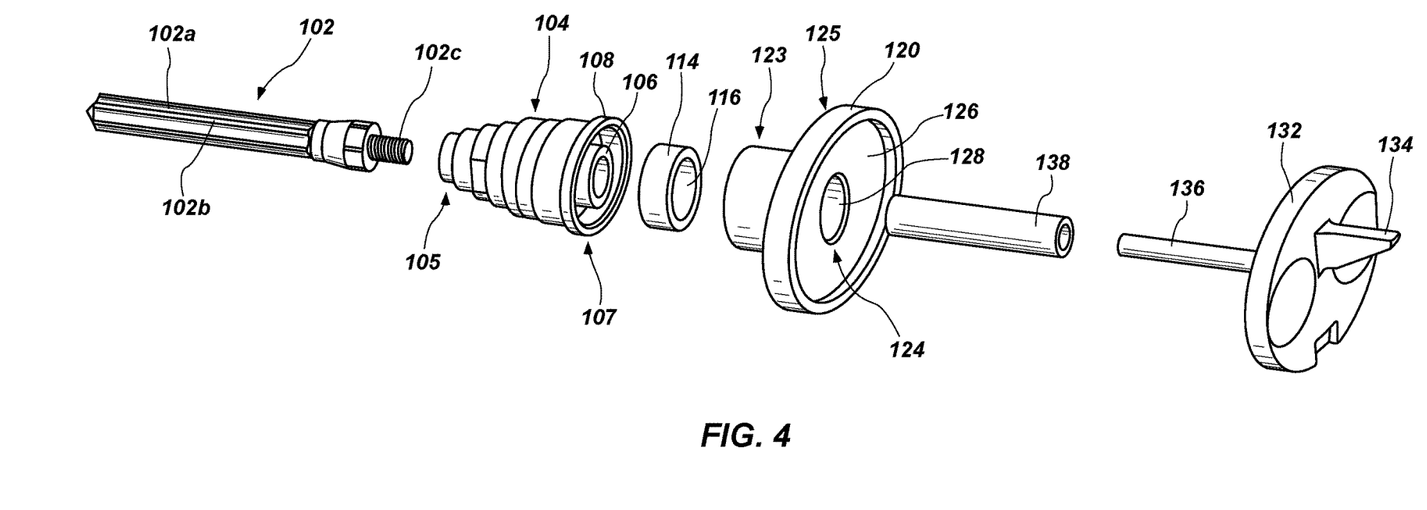
FIG. 4 is an exploded perspective view of the embodiment of FIG. 1.

Referring to FIGS. 1-6, the invention includes a revision stepped tibial implant 100. The implant 100 includes an implant stem 102 that is removably attached to a tibial sleeve 104. As shown in FIGS. 2 and 3, the stem 102 can be threadedly engaged with the tibial sleeve 104 allowing the stem 102 to be easily assembled with, or disengaged from, the tibial sleeve 104. This modularity between the stem 102 and the tibial sleeve 104 enable a surgeon or user to customize the sizes of stems 102 and tibial sleeve 104 to accommodate the specific need of each particular tibial implant. For example, the respective lengths and substantive diameters of the stem 102 and tibial sleeve 104 can be manufactured to a variety of different dimensions, enabling a surgeon to choose from an array of potential stems 102 and tibial sleeves 104, that are all equally engagable with one another, to ensure the best or most ideal fit for an intended patient or recipient.

Figure 7:
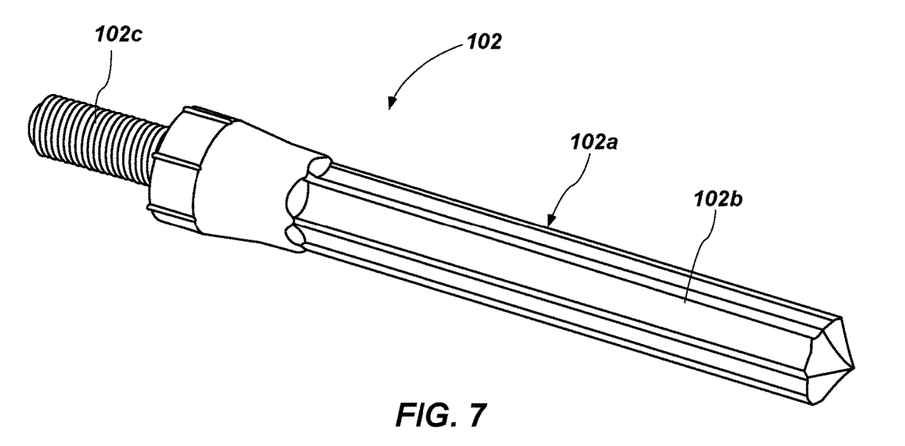
FIG. 7 is a perspective view of the stem of the present disclosure.
Figure 8:
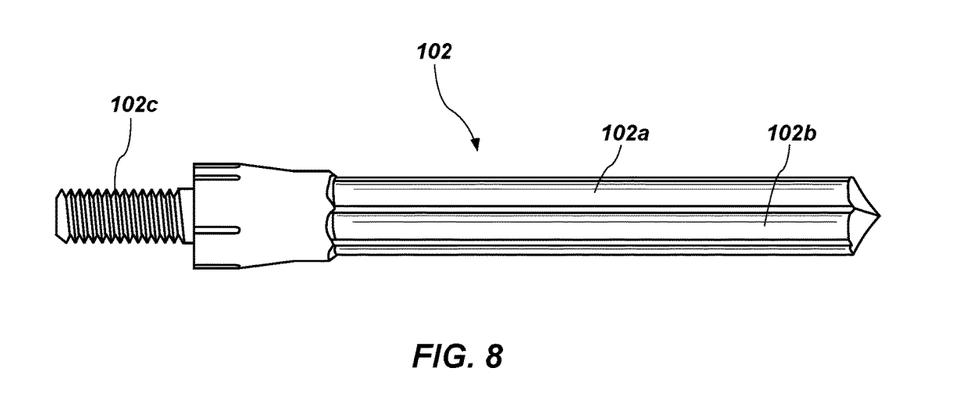
FIG. 8 is a side view of the stem of FIG. 7.

The stem 102, as seen in further detail in FIGS. 7 and 8, may include a spike portion 102a on the distal end 105 that is substantially straight and may include a plurality of ribs 102b extending radially from the spike portion 102a. This configuration of radially extending ribs 102b provides better fixation with surrounding bone of the tibia and reduces any tendency of the stem 102 to rotate once the stem is implanted in the tibial. On the distal end of the stem is a male threaded portion 102c which, as explained above, is dimensioned to threadedly mate with a female threaded portion 104a located on the distal end 105 of tibial sleeve 104. This threaded engagement enables different sizes of tibial sleeves 104 to mate with a variety of different sized stems 102.

The tibial sleeve 104 has a generally conical shape tapering down from the proximal end 107, the proximal end 107 having a larger diameter than the distal end 105. The outer surface of the tibial sleeve 104 includes a plurality of steps 104b that gradually reduce in diameter from the proximal end 107 of the tibial sleeve 104 to the distal end 105. The steps 104b on the outer surface of the tibial sleeve 104 facilitate improved grafting with the surrounding bone of the tibia after implantation of the tibial sleeve 104. This improved grafting can better secure the implant 100 in place and reduce the likelihood of complications or failure stemming from the unintentional displacement of the tibial implant 100, particularly when compared to a tibial implant having a substantially smooth outer surface.

As shown in FIGS. 2-5, the tibial sleeve 104 also includes an annular male portion 106 having a central bore 108 that may be coaxial with the tibial sleeve 104. The male end 106 extends from the proximal end 107 of the tibial sleeve 104, but does not extend in the proximal direction beyond an outer rim 110 of the tibial sleeve 104. The annular male portion or male end 106 may be unitary with the tibial sleeve 104, or may otherwise be fixedly attached to the tibial sleeve 104. A spacing between the male end 106 and the outer rim 110 creates an annular engagement groove 112.

The annular groove 112 is configured to receive an ring 114. The ring 114 may be designed and configured to fit securely around the male end 106 of the tibial sleeve 104 and be removably fixed to the male end 106 of the tibial sleeve 104, via a friction fit, cold weld or other desired securement mechanism.

Figure 6:
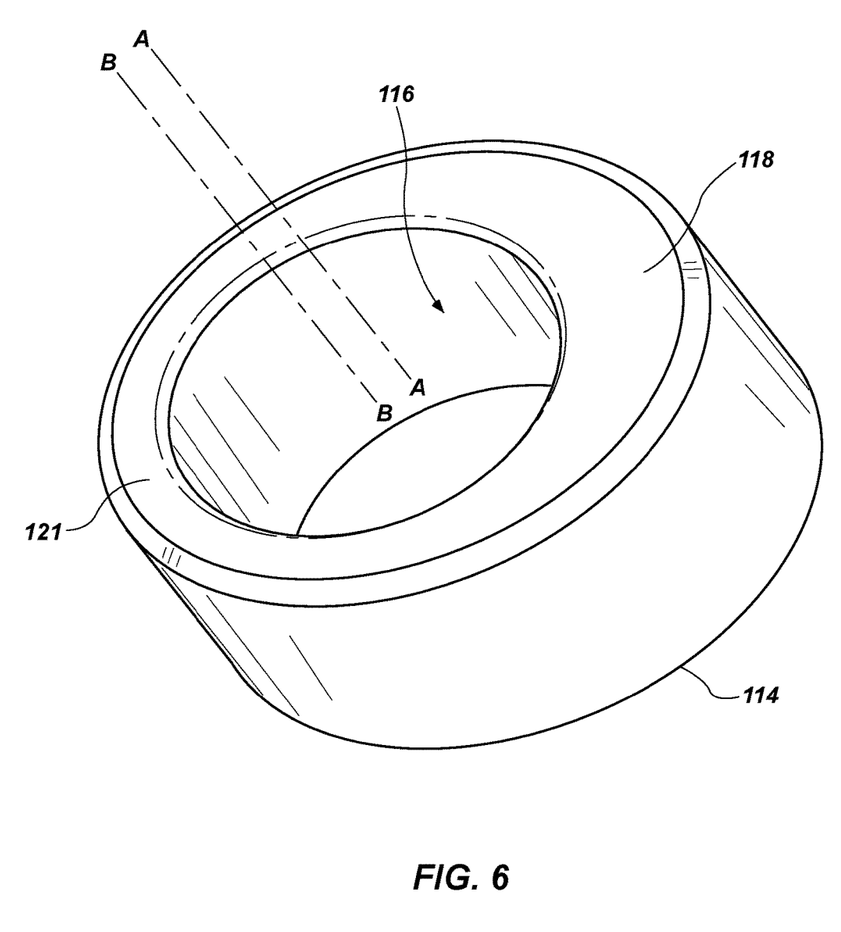
FIG. 6 is a perspective view of an example of an offset ring of the present disclosure.

As shown in FIG. 6 the ring 114 is cylindrical in shape, having a substantially circular cross-section. The offset ring also includes a bore 116 also having a substantially circular shape. The ring 114 may be an offset ring 114, wherein the bore 116, shown in FIG. 6, may be offset from the central axis, or center, of the offset ring 114, meaning that the central axis A-A of the offset ring 114 is not coaxial with the central axis B-B of the bore 116. The offset configuration of the bore 116 creates a first side 118 of the offset ring having a thicker (in a radial direction) cross-section that the cross-section of an opposing second side 121. For example, the first side 118 can have a thickness (in the radial direction) that is 1-4 mm greater than the thickness (in the radial direction) of the second side 120 of the offset ring 114. In another embodiment, the offset ring 114 may be configured with the bore 116 coaxial with the offset ring 114 itself, thus providing a symmetrical offset ring 114.

As shown in FIGS. 1-6, a base plate 120 includes, on the distal end 123, a female portion 122 that includes a counter-sunk bore 127 configured to receive the offset ring 114. The outer surface of the offset ring 114 is configured to engage and mate with the female portion 122 of the base plate 120, such that the female portion is removably fixed to the offset ring 114 via a friction fit, cold weld or other desired securement mechanism. The offset configuration of the bore 116 within the offset ring 114, enables the base plate 120 to correspondingly be offset with respect to the tibial sleeve 104 and stem 102.

The female portion 122 may be configured to receive both the offset ring 114 and the annular male portion 106 of the tibial sleeve 104. In an embodiment, the female portion 122 may receive only the offset ring 114. In another embodiment, the female portion 122 may receive only the annular male portion 106 of the tibial sleeve 104.

Figure 5:
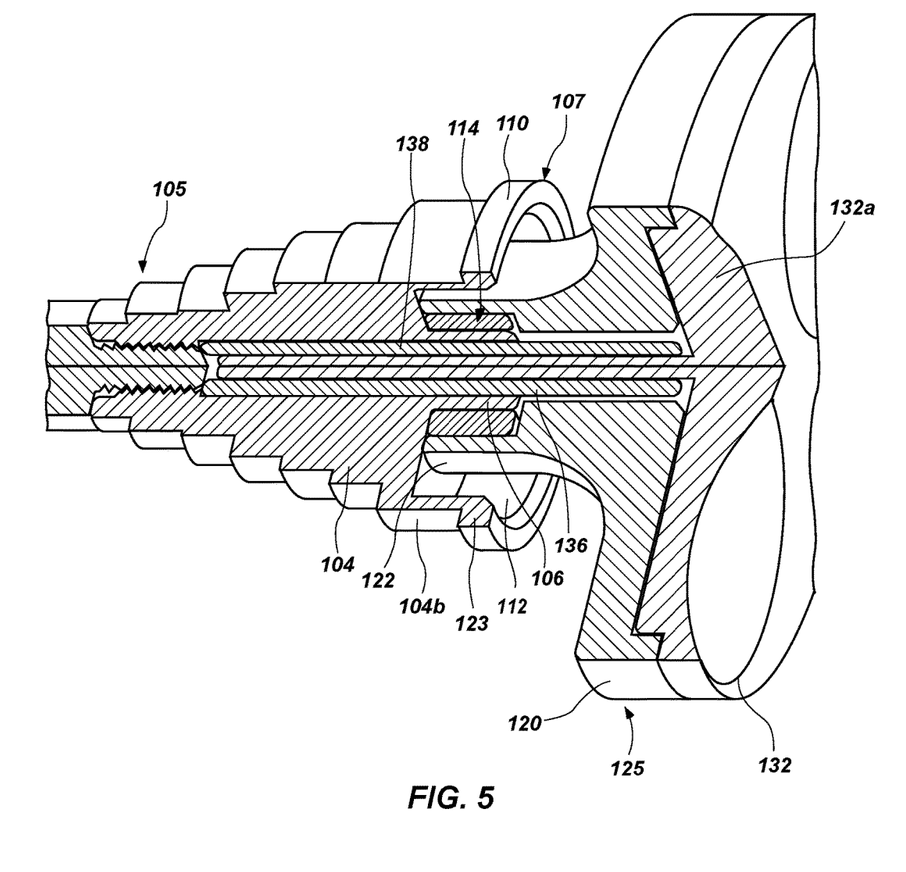
FIG. 5 is a partial cross-sectional view of the embodiment of FIG. 1.

As shown in FIG. 5, the annular engagement groove 112, or the space provided between the annular male portion, or male end, 106 and the outer rim 110 of the tibial sleeve 104, may be configured to receive not only the offset ring 114, but also the female portion 122 of the base plate 120. The annular engagement groove may comprise a distance between the male end 106 and the outer rim 110 that may vary depending on the desired application and sizes of the offset ring 114 and the base plate 120. For example, as shown in FIG. 5, the annular engagement groove 112 may comprise a distance between the male end 106 and the outer rim 110 that is greater than the distance required for the offset ring 114 and the female portion 122 of the base plate 120 to fit inside the annular engagement groove 112. The annular engagement groove 112 may be configured to accommodate an symmetrical offset ring 114, as described above, or an offset ring 114 having a first side that is thicker than a second side, as described above.

The removable engagement between the base plate 120 and the offset ring 114, can enable a surgeon or user to remove the base plate 120 from the tibial sleeve 104, and substitute a different base plate 120 and/or offset ring 114, without having to remove the tibial sleeve 104 and stem 102 from the tibia bone. The resulting modularity between the offset ring 114 and base plate 120, with respect to the tibial sleeve 104, enables the surgeon or user to change or modify the size, positioning (relative to the tibial sleeve 114 and stem 102), or type of base plate 120, without also removing tibial sleeve 104 and stem 102.

The proximal end 125 of the base plate 120 is configured with a counter-sunk tray portion 124. The tray portion 124 has a substantially planar central surface 126 having a central bore 128. The tray portion 124 also includes an outer rim 130 that extends around the perimeter of the central surface 126 and also extends in the proximal direction from the central surface 126. The tray portion 124 of the base plate 120 is configured to receive a platform 132. The platform 132 can be formed from a high strength plastic and can include various features or embodiments to accommodate various levels of restraint needed by a patient. For example, alternative platforms can be designed and used to accommodate a Posterior Cruciate (PS), Cruciate Retaining (CR), Constrained Condylar Knee (CCK) or hinge type platform.

As shown in FIGS. 1-5, the platform 132 can include a spike 134 that extends from a base portion 132a of the platform 132 in a proximal direction, and a post 136 extends in an opposite distal direction from the spike 134. Although the base portion 132a of the platform can be made of a plastic material, the post 136 can be made from a metal material, for added strength, which can extend through the base portion 132a of the platform 132 and into the spike 134, providing strength and support to the spike 134 during use. The spike 134 may vary in size and length depending on the level of restraint needed by the patient. Additionally, the location of the spike 134 on the platform 132 can also very, for example, the spike 134 can be offset from the center of the platform, as shown in FIGS. 2-5, or the spike can be centered and substantially coaxial with the post 136.

The post 136 extends through the bore 128 of the base plate 120, through the offset ring 114 and into the central bore 108 of the male end 106 of the tibial sleeve 104. The central bore of the tibial sleeve can be sized to retain the post 136 and provide strength and stability to the platform 132, via the post. The post 132 is removable from the central bore 108 of the tibial sleeve 104, to enable simple and easy removal and replacement of the platform 132, without requiring a corresponding removal of the tibial sleeve 104 and stem 102.

As discussed above, the tray portion 124 of the base plate 120 is configured to receive the platform 132, and the platform 132 is configured to engage with a corresponding femoral implant (not shown), thus completing a total knee replacement implant. The tibial implant 100 can be a fixed bearing system, where the platform 132 is fixed to the tray 124, such that the platform can not rotate with respect to the tray 124 or base plate 120. In the fixed bearing configuration the platform can be cold welded to the tray 124 or fixed using another desired fixation mechanism.

Alternatively, the tibial implant 100 can be a mobile bearing system, where the platform 132 is rotatable with respect to the tray 124 and base plate 120. As shown FIGS. 2-5, the post 136 of the platform can be received within a bushing 138, where the bushing 138 is also received within the bore 128 of the base plate 120 and the central bore 108 of the tibial implant 104. The bushing 138 is sized to the central bore 108 of the tibial sleeve 104 without any lateral movement, thus providing lateral stability to the post 136 and platform 132, while still maintaining smooth rotatability of the platform with respect to the base plate and tibial sleeve 104. The bushing 138 reduces the friction of the rotating post 136, thus improving the life and functionality of both the post 136 and the tibial sleeve 104.

In alternative embodiments, a fixed bearing platform 132 can include a shorter post and a bushing 138 is unnecessary, as there is no rotation of the platform 132. Thus, alternative tibial sleeves can also be utilized, having varying sized central bores 108 to compensate for the use of a bushing 138 in a mobile bearing configuration or the absence of a bushing 138 in a fixed bearing configuration.

In other exemplary embodiments and similar to the size versatility of the stem 102, tibial sleeve 104, and offset ring 114, the blase plate 120 and platform 132 can also be made to different lengths, and diameters to accommodate the varying needs of patients and the necessary level of constraint needed for the tibial implant 100. The varying sizes of all of the different components referenced above, and the above described modularity of the corresponding components, can be interchangeably mixed and matched, creating a matrix of component configurations and possibilities. Of particular benefit is the ability to change the offset ring 114, base plate 120 and/or platform 132 without removing the stem 102 and tibial sleeve 104, thus preserving the integrity of the tibial bone surrounding the stem 102 and tibial sleeve 104.

Figure 9:
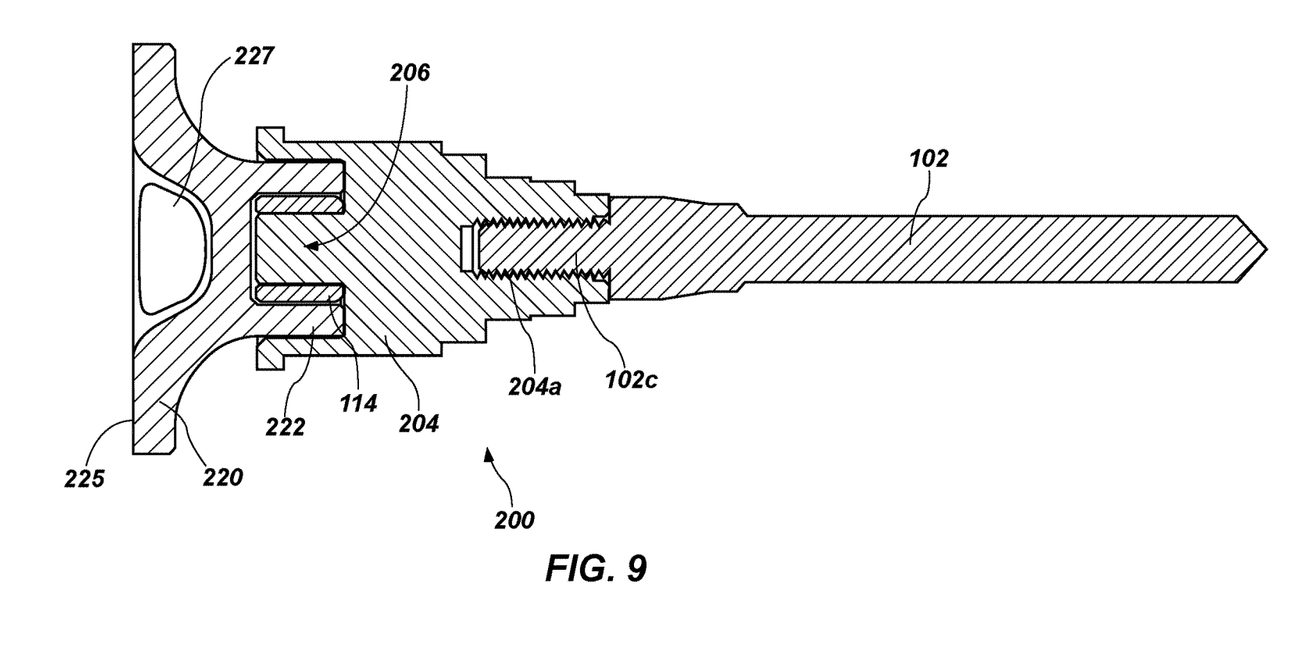
FIG. 9 is a cross-sectional view of another embodiment of the present disclosure.
Figure 10:
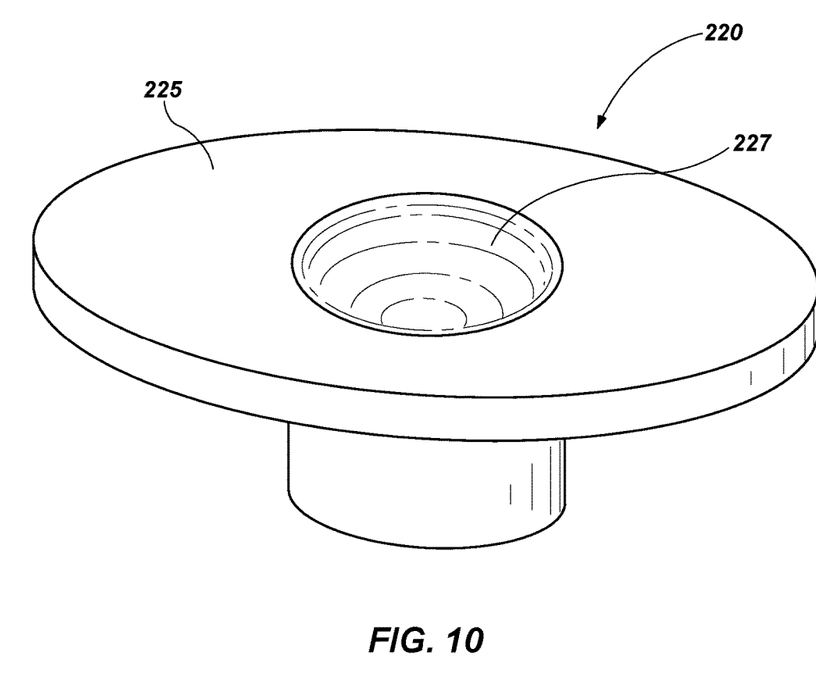
FIG. 10 is a perspective view of the base plate of the embodiment of FIG. 9.

In another exemplary embodiment, as shown in FIGS. 9 and 10, a tibial implant 200 is illustrated utilizing the same modularity characteristics discussed above with respect to tibial implant 100. For example, the same stem 102 having a male threaded portion 102c, mates with a tibial sleeve 204 via a female threaded portion 204a. Tibial sleeve 204 has the same features as the corresponding tibial sleeve 104, except the male end 206 of the tibial sleeve 204 does not include a central bore. However, the male end 206 of the tibial sleeve 204 is still configured to receive the offset ring 114. The tibial implant 200 also includes a base plate 220 having the same type of female end 222 as the corresponding base plate 120. The base plate 220 having the same type of female end 222 as the base plate 120, illustrates the common modularity of the components described above with respect to tibial implant 100 and tibial implant 200.

The base plate 220 is different from base plate 120 in that there is no bore that extends through the base plate 220, or tray portion 124 of the base plate 120. Instead, base plate 220 includes a substantially planar proximal surface 225 having a central depression 227. The proximal surface can be fixed to a corresponding platform (not shown) using cement, glue or other desired adhesive of attachment mechanism. The depression 224 can receive a post extending from the platform, and the post may be shorter that the post 136 of platform 132 described above.

Figure 11:
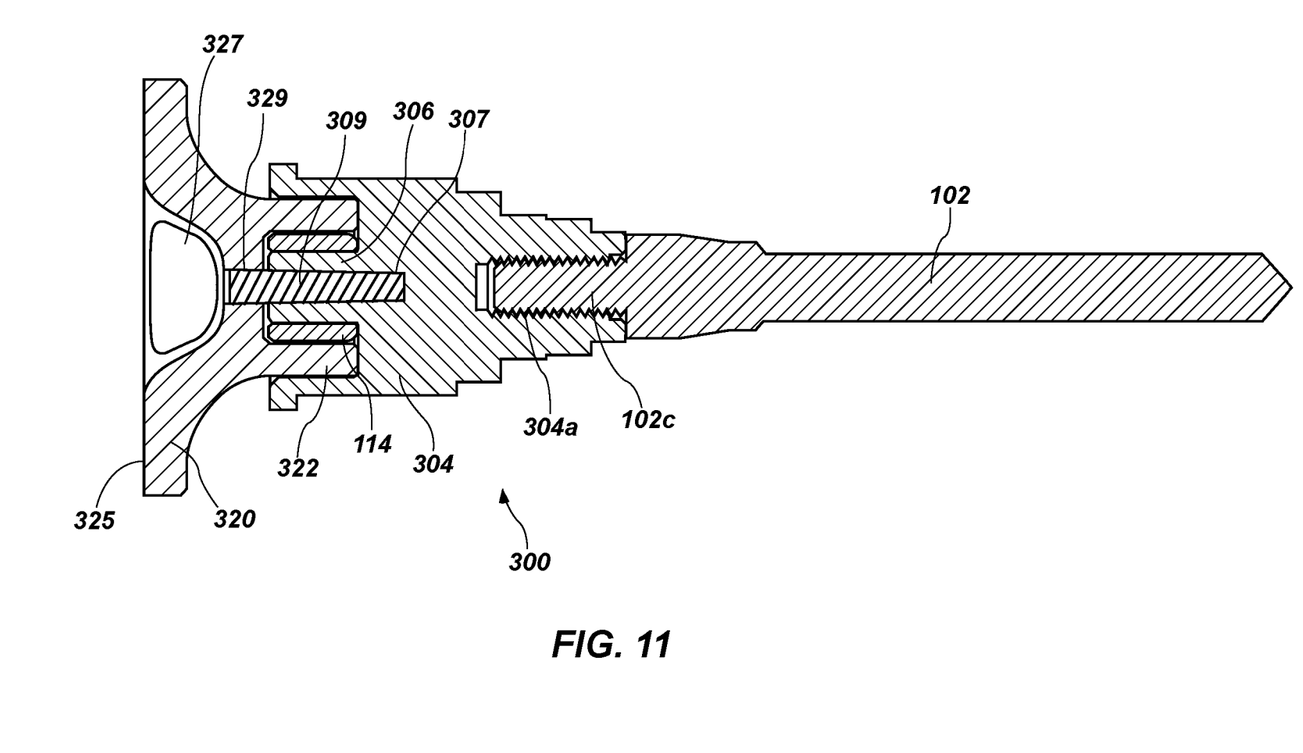
FIG. 11 is a cross-section view of an alternative embodiment of the present disclosure.

In another exemplary embodiment, as shown in FIG. 11, a tibial implant 300 is illustrated utilizing the same modularity characteristics discussed above with respect to tibial implant 100. For example, the same stem 102 having a male threaded portion 102c, mates a tibial sleeve 304 via a female threaded portion 304a. Tibial sleeve 304 has the same features as the corresponding tibial sleeve 104, except the male end 306 of the tibial sleeve 204 does not include a central bore, but instead includes a threaded bore 307 which is configured to threadedly mate with a set screw 309. A male end 306 of the tibial sleeve 304 is still configured to receive the offset ring 114, in the same way tibial sleeves 104 and 204 also receive the offset ring 114.

The tibial implant 300 also includes a base plate 320 having the same type of female end 322 as the corresponding base plate 120. The base plate 220 having the same type of female end 222 as the base plate 120, illustrates the common modularity of the components described above with respect to tibial implant 100 and tibial implant 200.

The base plate 320 is different from base plate 220 in that there is a central bore 329 that is configured to receive the set screw 307. Thus the set screw 307 can secure the base plate 320 to tibial sleeve 304 and add strength and stability to the connection, beyond the use of a cold weld or press fit connection. Base plate 320 also includes a substantially planar proximal surface 325 having a central depression 327. The proximal surface can be fixed to a corresponding platform (not shown) using cement, glue or other desired adhesive or attachment mechanism. The depression 324 can receive a post extending from the platform, and the post may be shorter than the post 136 of platform 132 described above.

The tibial sleeves and base plates of the present disclosure above may be formed of a metal material (or other desired bio compatible material) having a non-smooth surface (i.e. porous coating, trabecular metal, gription, bio-foam or any other suitable non-smooth surface) which may be ideal for an un-cemented configuration, or a substantially smooth outer surface when used in conjunction with a cement product.

In accordance with the features and combinations described above, a tibial implant may comprise:
 a stem;
 a tibial sleeve having a proximal end and a distal end, wherein the proximal end includes an annular male portion;

an offset ring having a central bore that is offset from the center of the offset ring, wherein the bore of the offset ring receives the annular male portion of the tibial sleeve; and a base plate having a proximal end and a distal end, wherein the distal end of the base plate forms a female portion, and wherein the female portion receives both the offset ring and the male portion of the tibial sleeve.

The tibial sleeve including a stepped exterior surface.

The offset ring being removably engaged with the tibial sleeve.

The base plate being removably engaged with the offset ring and tibial sleeve.

The stem being threadedly engaged with the tibial sleeve.

The tibial sleeve also including an outer rim that extends from the proximal end of the tibial sleeve and surrounds the annular male portion.

The outer rim does not extend further in the proximal direction than the annular male portion.

The offset ring also includes a first side of the bore and a second side of the bore, the second side opposite the first side, wherein the first side is 1 to 4 mm thicker in a radial direction than the second side.

The tibial implant also includes a platform having a base portion and a post extending in a distal direction from the base portion, wherein the post extends through a bore in the base plate and a central bore in the tibial sleeve.

The platform being removably engaged to the base plate and tibial sleeve.

The platform being rotatable with respect to the base plate and tibial sleeve.

The platform is not rotatable with respect to the base plate and tibial sleeve.

In accordance with the features and combinations described above, a tibial implant may comprise:
  a stem;
  a tibial sleeve having a proximal end and a distal end, wherein the proximal end includes an annular male portion;
  a base plate having a proximal end and a distal end, wherein the distal end of the base plate forms a female portion, and wherein the female portion receives the male portion of the tibial sleeve,
  a platform having a base portion and a post extending in a distal direction from the base portion, wherein the post extends through a bore in the base plate and a central bore in the tibial sleeve.

In accordance with the features and combinations described above, a tibial implant may comprise:
  a stem;
  a tibial sleeve having a proximal end and a distal end, wherein the proximal end includes an annular male portion, the tibial sleeve also including a stepped exterior surface and an outer rim that extends from the proximal end of the tibial sleeve and surrounds the annular male portion, the outer rim not extending further in the proximal direction than the annular male portion;
  an offset ring having a central bore that is offset from the center of the offset ring, wherein the bore of the offset ring receives the annular male portion of the tibial sleeve;
  a base plate having a proximal end and a distal end, wherein the distal end of the base plate forms a female portion, and wherein the female portion receives both the offset ring and the male portion of the tibial sleeve; and
  a platform having a base portion and a post extending in a distal direction from the base portion, wherein the post extends through a bore in the base plate and a central bore in the tibial sleeve;
  wherein the offset ring is removably engaged with the tibial sleeve, and the base plate is removably engaged with the tibial sleeve.

In accordance with the features and combinations described above, a method of utilizing a tibial implant may comprise:
  inserting a stem into a tibial bone;
  inserting a tibial sleeve into the tibial bone, the tibial sleeve having a proximal end and a distal end, wherein the proximal end includes an annular male portion;
  connecting a base plate to the tibial sleeve, the base plate having a proximal end and a distal end, wherein the distal end of the base plate forms a female portion, and wherein the female portion receives the male portion of the tibial sleeve when connected; and
  connecting a platform to the tibial sleeve, the platform having a base portion and a post extending in a distal direction from the base portion, wherein the post extends through a bore in the base plate and a central bore in the tibial sleeve when connected.

The method may also include: connecting an offset ring to the tibial sleeve, the offset ring having a central bore that is offset from the center of the offset ring, wherein the bore of the offset ring receives the annular male portion of the tibial sleeve when connected.

The method may also include: removing the offset ring from connection with the tibial sleeve without removing the tibial sleeve from the tibial bone.

The method may also include: removing the base plate from connection with the tibial sleeve without removing the tibial sleeve from the tibial bone.

The method may also include: removing the platform from connection with the tibial sleeve without removing the tibial sleeve from the tibial bone.

The platform is not rotatable with respect to the base plate and tibial sleeve.

The method may also include: removing the platform from connection with the tibial sleeve without removing the tibial sleeve from the tibial bone; and The method may also include: connecting a replacement platform to the tibial sleeve, wherein the replacement platform is rotatable with respect to the base plate and tibial sleeve.

It is to be understood that the above-described arrangements are only illustrative of the application of the principles of the present disclosure. Numerous modifications and alternative arrangements may be devised by those skilled in the art without departing from the spirit and scope of the present disclosure are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A tibial implant comprising:
  a stem;
  a tibial sleeve having a proximal end and a distal end, wherein the proximal end includes an annular male portion;

an offset ring having a central bore that is offset from the center of the offset ring, wherein the bore of the offset ring receives the annular male portion of the tibial sleeve; and a base plate having a proximal end and a distal end, wherein the distal end of the base plate forms a female portion, and wherein the female portion receives both the offset ring and the annular male portion of the tibial sleeve.

2. The tibial implant of claim 1, wherein the tibial sleeve includes a stepped exterior surface.

3. The tibial implant of claim 1, wherein the offset ring is removably engaged with the tibial sleeve.

4. The tibial implant of claim 1, wherein the base plate is removably engaged with the offset ring and tibial sleeve.

5. The tibial implant of claim 1, wherein the stem is threadedly engaged with the tibial sleeve.

6. The tibial implant of claim 1, wherein the tibial sleeve also includes an outer rim that extends from the proximal end of the tibial sleeve and surrounds the annular male portion.

7. The tibial implant of claim 6, wherein the outer rim does not extend further in the proximal direction than the annular male portion.

8. The tibial implant of claim 1, further comprising:
a platform having a base portion and a post extending in a distal direction from the base portion, wherein the post extends through a bore in the base plate and a central bore in the tibial sleeve.

9. The tibial implant of claim 8, wherein the platform is removably engaged to the base plate and tibial sleeve.

10. The tibial implant of claim 8, wherein the platform is rotatable with respect to the base plate and tibial sleeve.

11. The tibial implant of claim 8, wherein the platform is not rotatable with respect to the base plate and tibial sleeve.

12. The tibial implant of claim 1, wherein the offset ring includes a first side and a second side, the second side opposite the first side, wherein the first side is 1 to 4 mm thicker in a radial direction than the second side.

13. A tibial implant comprising:
a stem;
a tibial sleeve having a proximal end and a distal end, wherein the proximal end includes an annular male portion;
a base plate having a proximal end and a distal end, wherein the distal end of the base plate forms a female portion, and wherein the female portion receives the male portion of the tibial sleeve; and
a platform having a base portion and a post extending in a distal direction from the base portion, wherein the post extends through a bore in the base plate and a central bore in the tibial sleeve.

14. The tibial implant of claim 13, further comprising:
an offset ring having a central bore that is offset from the center of the offset ring, wherein the bore of the offset ring receives the annular male portion of the tibial sleeve.

15. The tibial implant of claim 14, wherein the female portion of the base plate receives the offset ring.

16. The tibial implant of claim 14, wherein the offset ring is removably engaged with the tibial sleeve.

17. The tibial implant of claim 14, wherein the offset ring includes a first side of the bore and a second side of the bore, opposite the first side, wherein the first side is 1 to 4 mm thicker in a radial direction than the second side.

18. The tibial implant of claim 13, wherein the tibial sleeve includes a stepped exterior surface.

19. The tibial implant of claim 13, wherein the base plate is removably engaged with the tibial sleeve.

20. The tibial implant of claim 13, wherein the stem is threadedly engaged with the tibial sleeve.

21. The tibial implant of claim 13, wherein the tibial sleeve also includes an outer rim that extends from the proximal end of the tibial sleeve and surrounds the annular male portion.

22. The tibial implant of claim 21, wherein the outer rim does not extend further in the proximal direction than the annular male portion.

23. The tibial implant of claim 13, wherein the platform is removably engaged to the base plate and tibial sleeve.

24. The tibial implant of claim 13, wherein the platform is rotatable with respect to the base plate and tibial sleeve.

25. The tibial implant of claim 13, wherein the platform is not rotatable with respect to the base plate and tibial sleeve.

26. A tibial implant comprising:
a stem;
a tibial sleeve having a proximal end and a distal end, wherein the proximal end includes an annular male portion, the tibial sleeve also including a stepped exterior surface and an outer rim that extends from the proximal end of the tibial sleeve and surrounds the annular male portion, the outer rim not extending further in the proximal direction than the annular male portion;
an offset ring having a central bore that is offset from the center of the offset ring, wherein the bore of the offset ring receives the annular male portion of the tibial sleeve;
a base plate having a proximal end and a distal end, wherein the distal end of the base plate forms a female portion, and wherein the female portion receives both the offset ring and the male portion of the tibial sleeve; and
a platform having a base portion and a post extending in a distal direction from the base portion, wherein the post extends through a bore in the base plate and a central bore in the tibial sleeve;
wherein the offset ring is removably engaged with the tibial sleeve, and the base plate is removably engaged with the tibial sleeve.

27. A method of utilizing a tibial implant, comprising:
inserting a stem into a tibial bone;
inserting a tibial sleeve into the tibial bone, the tibial sleeve having a proximal end and a distal end, wherein the proximal end includes an annular male portion;
connecting a base plate to the tibial sleeve, the base plate having a proximal end and a distal end, wherein the distal end of the base plate forms a female portion, and wherein the female portion receives the male portion of the tibial sleeve when connected; and
connecting a platform to the tibial sleeve, the platform having a base portion and a post extending in a distal direction from the base portion, wherein the post extends through a bore in the base plate and a central bore in the tibial sleeve when connected.

28. The method of claim 27, further comprising:
connecting an offset ring to the tibial sleeve, the offset ring having a central bore that is offset from the center of the offset ring, wherein the bore of the offset ring receives the annular male portion of the tibial sleeve when connected.

29. The method of claim 28, further comprising:
removing the offset ring from connection with the tibial sleeve without removing the tibial sleeve from the tibial bone.

30. The method of claim 27, further comprising:
removing the base plate from connection with the tibial sleeve without removing the tibial sleeve from the tibial bone.

31. The method of claim 27, further comprising:
removing the platform from connection with the tibial sleeve without removing the tibial sleeve from the tibial bone.

32. The method of claim 27, wherein the platform is not rotatable with respect to the base plate and tibial sleeve.

33. The method of claim 32, further comprising:
removing the platform from connection with the tibial sleeve without removing the tibial sleeve from the tibial bone; and
connecting a replacement platform to the tibial sleeve, wherein the replacement platform is rotatable with respect to the base plate and tibial sleeve.

34. A tibial implant comprising:
a stem;
a tibial sleeve having a proximal end and a distal end, wherein the proximal end includes an annular male portion;
a ring having a central bore, wherein the bore of the ring receives the annular male portion of the tibial sleeve; and
a base plate having a proximal end and a distal end, wherein the distal end of the base plate forms a female portion, and wherein the female portion receives both the ring and the annular male portion of the tibial sleeve.

35. The tibial implant of claim 34, wherein the ring is an offset ring having a central bore that is offset from the center of the offset ring.

36. The tibial implant of claim 34, wherein the annular male portion is unitary with the sleeve.

37. A tibial implant comprising:
a stem;
a tibial sleeve having a proximal end and a distal end, wherein the proximal end includes an annular male portion;
an offset ring having a central bore that is offset from the center of the offset ring, wherein the bore of the offset ring receives the annular male portion of the tibial sleeve; and
a base plate having a proximal end and a distal end, wherein the distal end of the base plate forms a female portion, and wherein the female portion receives the annular male portion of the tibial sleeve.

38. The tibial implant of claim 37, wherein the annular male portion is unitary with the sleeve.

39. A tibial implant comprising:
a stem;
a tibial sleeve having a proximal end and a distal end, wherein the proximal end includes an annular male portion;
an offset ring having a central bore that is offset from the center of the offset ring, wherein the bore of the offset ring receives the annular male portion of the tibial sleeve; and
a base plate having a proximal end and a distal end, wherein the distal end of the base plate forms a female portion, and wherein the female portion receives the offset ring.

40. The tibial implant of claim 39, wherein the annular male portion is unitary with the sleeve.

* * * * *